United States Patent [19]
Doebert et al.

[11] Patent Number: 5,579,366
[45] Date of Patent: *Nov. 26, 1996

[54] LINE DETECTOR CAMERA FOR EMPLOYMENT IN, PARTICULARLY, DENTAL X-RAY DIAGNOSTICS INSTALLATIONS

[75] Inventors: Michael Doebert, Lorsch; Werner Guenther, Bensheim; Ulrich Schulze-Ganzlin, Lorsch; Josef Ploetz; Erich Heubeck, both of Bensheim, all of Germany

[73] Assignee: Siemens Aktiengesellschaft, Munich, Germany

[ * ] Notice: The term of this patent shall not extend beyond the expiration date of Pat. No. 5,511,106.

[21] Appl. No.: 268,119

[22] Filed: Jul. 6, 1994

[30] Foreign Application Priority Data

Jul. 6, 1993 [DE] Germany .................... 43 22 484.9

[51] Int. Cl.⁶ .................................... H01J 31/49
[52] U.S. Cl. .................................... 378/189; 378/39
[58] Field of Search ............... 378/38, 39, 40, 378/62, 19, 20, 98.8, 189, 190, 191; 250/370.09, 370.11; 257/433, 434, 81, 82

[56] References Cited

U.S. PATENT DOCUMENTS

| | | | |
|---|---|---|---|
| 4,811,372 | 3/1989 | Doebert et al. | 378/39 |
| 4,823,369 | 4/1989 | Guenther et al. | 378/22 |
| 4,870,673 | 9/1989 | Adler et al. | 378/148 |
| 4,878,234 | 10/1989 | Pfeiffer et al. | 378/40 |
| 4,945,731 | 7/1989 | Vidmar et al. | 378/98 |
| 5,012,498 | 4/1991 | Cuzin et al. | 378/19 |
| 5,177,776 | 1/1993 | Ohmori et al. | 378/19 |

FOREIGN PATENT DOCUMENTS

| | | |
|---|---|---|
| 0166567 | 1/1986 | European Pat. Off. . |
| 0194743 | 9/1986 | European Pat. Off. . |
| WO8100457 | 2/1981 | WIPO . |

OTHER PUBLICATIONS

"Halbleiterbildaufnehmer für die Röntggentechnik," Rozière et al, Elektronik, vol. 17, No. 22 Aug. 1986 (pp. 62–66).

Primary Examiner—Don Wong
Attorney, Agent, or Firm—Hill, Steadman & Simpson

[57] ABSTRACT

A line detector camera suitable for employment in a dental x-ray diagnostics apparatus contains an x-ray-sensitive detector held in a housing, the detector containing a plurality of detector elements that are arranged to form one or more lines, and having contacts connected to control lines that are in turn connected to a connector part. The connector part makes both electrical and mechanical connection in a releasable manner to a correspondingly fashioned holder of the x-ray diagnostics apparatus.

14 Claims, 6 Drawing Sheets

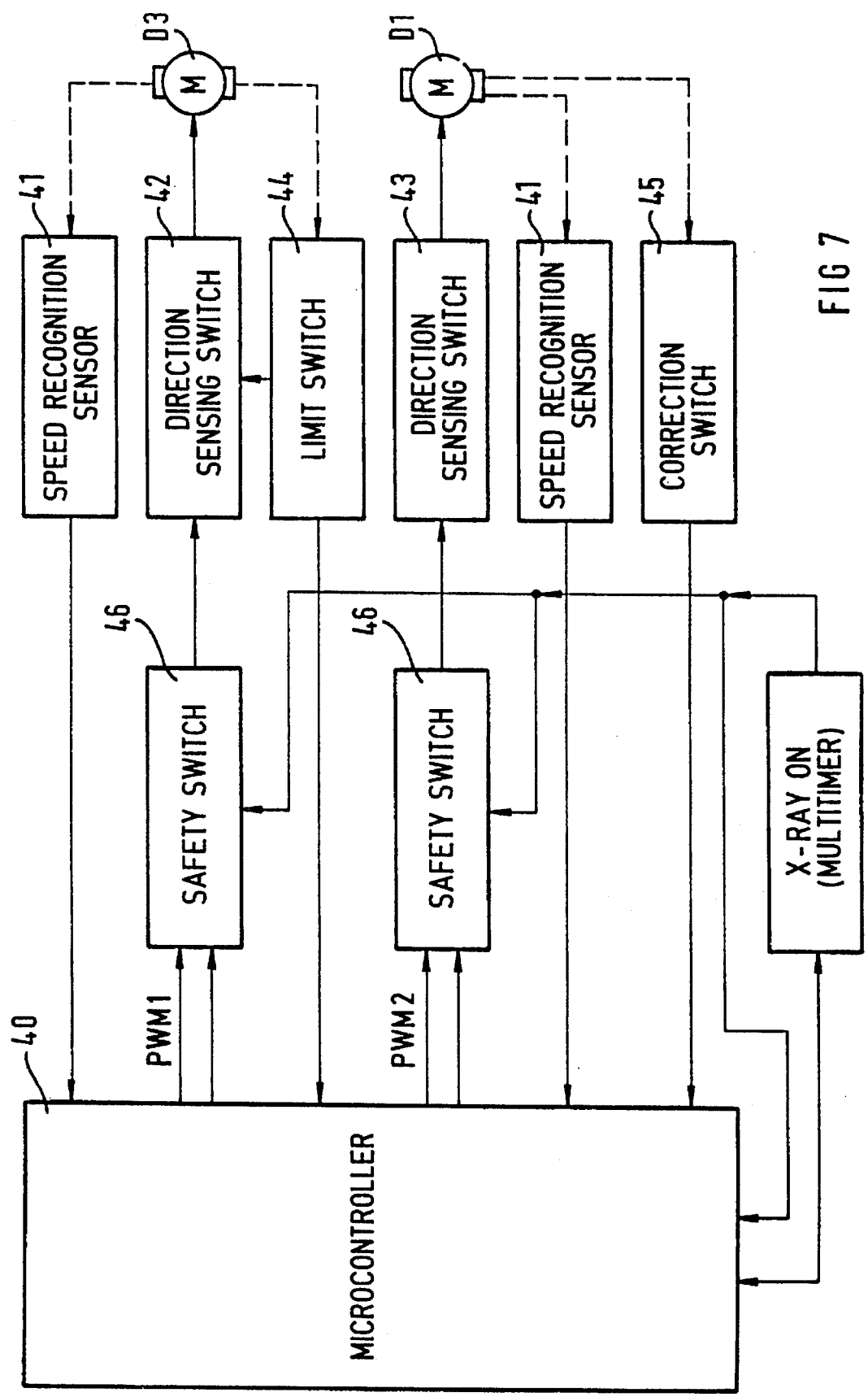

5,579,366

LINE DETECTOR CAMERA FOR EMPLOYMENT IN, PARTICULARLY, DENTAL X-RAY DIAGNOSTICS INSTALLATIONS

BACKGROUND OF THE INVENTION

1. Field of the Invention

The present invention is directed to a line detector camera of the type suitable for employment in dental x-ray diagnostics installations.

2. Description of the Prior Art

In x-ray diagnostics installations, it is standard to arrange a cassette for acceptance of an x-ray film that is matched to the subject in front of the body part of a patient (tooth, jaw, skull, memory) to be trans-irradiated. When, for example, one wishes to produce a panorama (PAN) exposure of the jaw, a different film cassette having a different film format is required than, for example, when a remote x-ray (ceph) exposure is to be produced of the skull of a patient.

It is known in dental x-ray technology to alternatively be able to make PAN and ceph exposures with the same basic apparatus. For ceph-exposures, a boom having a skull holder and a film cassette appropriately matched to the subject is attached to the basic apparatus. As already mentioned, different film cassettes and film formats are required for these two types of exposure as described in European Applications 0 229 308 and 0 262 522.

Dental x-ray diagnostics installations are likewise known wherein a radiation-sensitive sensor, for example a CCD sensor, having a scintillation layer arranged in front thereof, can be employed instead of an x-ray film. Apparatuses of this type which have been disclosed heretofore, however, are only suitable for the production of PAN exposures (European Application 0 279 294).

SUMMARY OF THE INVENTION

An object of the present invention is to provide a line detector camera that can be employed for exposures of different body parts and that, in particular, can be employed both for PAN as well as for ceph exposures.

The above object is achieved in accordance with the principles of the present invention in a line detector camera containing electrical and mechanical connection means for making a releasable connection to a corresponding holder of a PAN and/or ceph apparatus. Dependent on whether the x-ray diagnostics installation is provided for one or the other or for both types of exposures, the aforementioned exposures can be produced with only one camera. In the case of a PAN exposure, the camera can be vertically secured to the holder; in the case of a ceph exposure, it can be vertically or horizontally secured to the holder. By contrast to the two differently fashioned cassettes and cassette holders previously required, only a single camera, and respective holders for the two types of exposures which are structurally identical, are provided.

DESCRIPTION OF THE DRAWINGS

FIG. 7 shows a block circuit diagram for driving the adjusting motors in the above embodiments.

DESCRIPTION OF THE PREFERRED EMBODIMENTS

Figure 1:
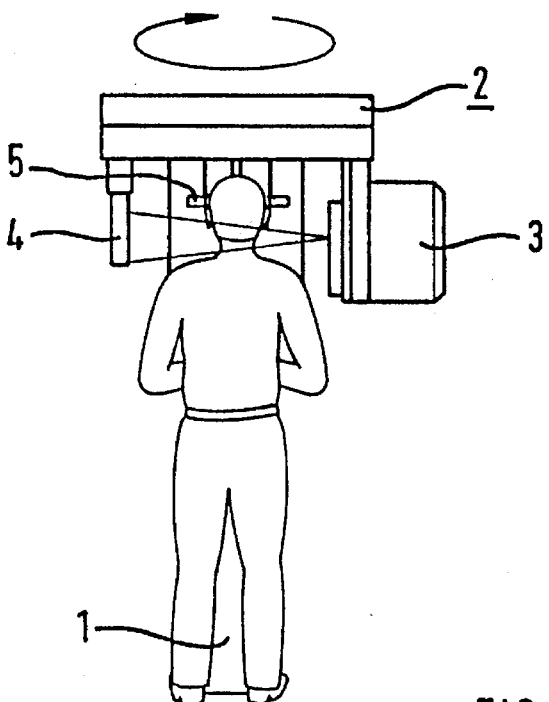
FIG. 1 is a schematic illustration of a dental x-ray diagnostics apparatus for producing PAN exposures constructed in accordance with the principles of the present invention.

FIG. 1 shows a schematic illustration of a dental x-ray diagnostics apparatus for producing panorama tomograms, referred to below abbreviated as PAN exposures. The apparatus contains a height-adjustable carrying column 1 at which a rotatory unit 2 is held, forming a carrier for an x-ray source 3 and an x-ray line camera 4 diametrically relative thereto.

The installation also has a (first) head-holder 5 and positioning means with which the patient's head can be fixed in a defined position in a known way. The structure as well as adjustment possibilities of the rotatory unit and of the head-holder and positioning means are known and are disclosed, for example, in European Application 0 229 308.

Figure 2:
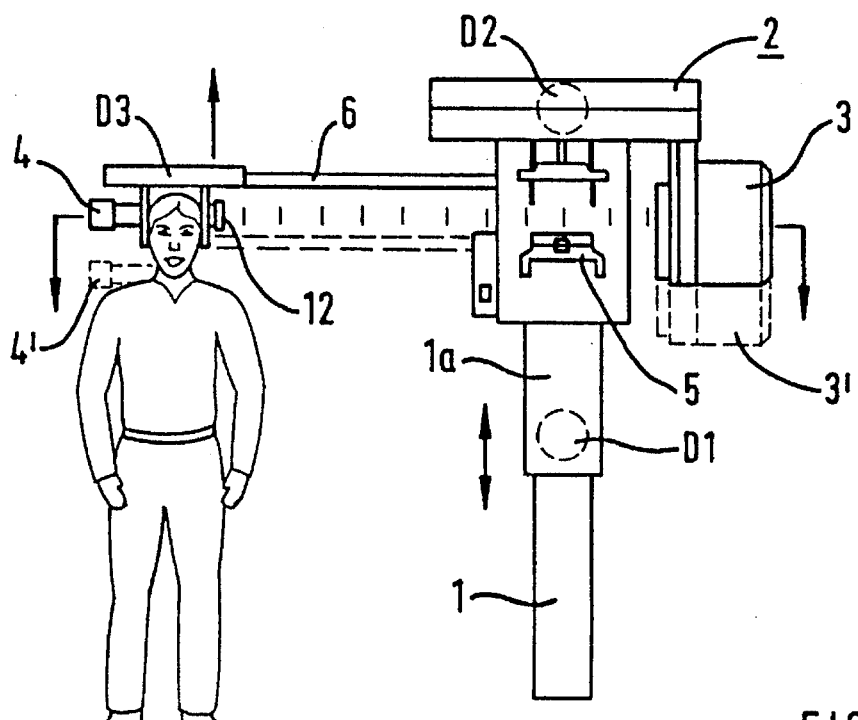
FIG. 2 shows the apparatus of FIG. 1 modified for producing ceph exposures.

FIG. 2 shows the same basic apparatus composed of height-adjustable carrying column 1, rotatory unit 2 and x-ray radiator 3, but supplemented by a device adaptable at the apparatus with which remote skull exposures, referred to below abbreviated as ceph exposures, can be produced. Before this apparatus is set forth in greater detail, it should be mentioned that the carrying column 1 is height-adjustable with a drive D1 in the indicated arrow direction, and that the rotatory unit 2 can be turned and pivoted with one or more drives D2 in order to be able to make a PAN exposure. Details with respect thereto are disclosed in the aforementioned European Application 0 229 308.

Figure 3:
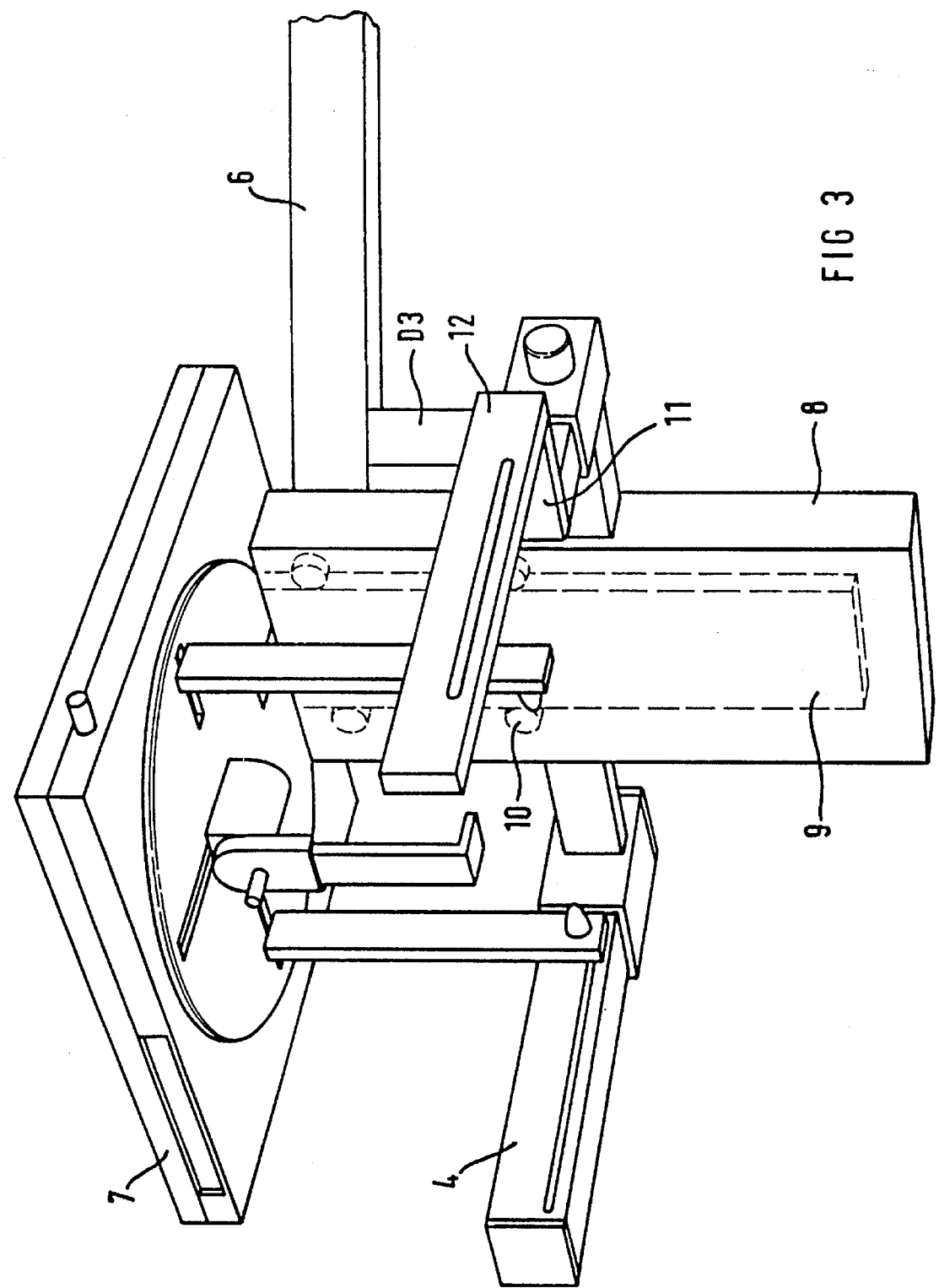
FIG. 3 is a schematic illustration of the apparatus provided for ceph exposures.

FIG. 3 shows a schematic illustration of the aforementioned device for producing ceph exposures.

A boom 6 that carries a (second) head-holder 7 and positioning means is secured to the height-adjustable part 1a of the carrying column 1 (FIG. 2). The boom 6 has a housing 8 at which a blade 9 that carries the head-holder 7 and positioning means is adjustably seated by guide rollers 10 arranged in the housing 8. The line camera 4 is connected by a traverse element 11 to a pre-diaphragm 12 that serves the purpose of again exactly adjusting the fan beam (already limited in a known way by the secondary diaphragm neighboring the x-ray source 3) onto the slot width and length of the line camera, to be set forth in greater detail below.

By contrast to the exemplary embodiment of FIG. 1, the line camera in the embodiment of FIG. 2 is not vertically arranged but is horizontally arranged. A correspondingly fashioned holder is shown in FIG. 5.

Figure 4:
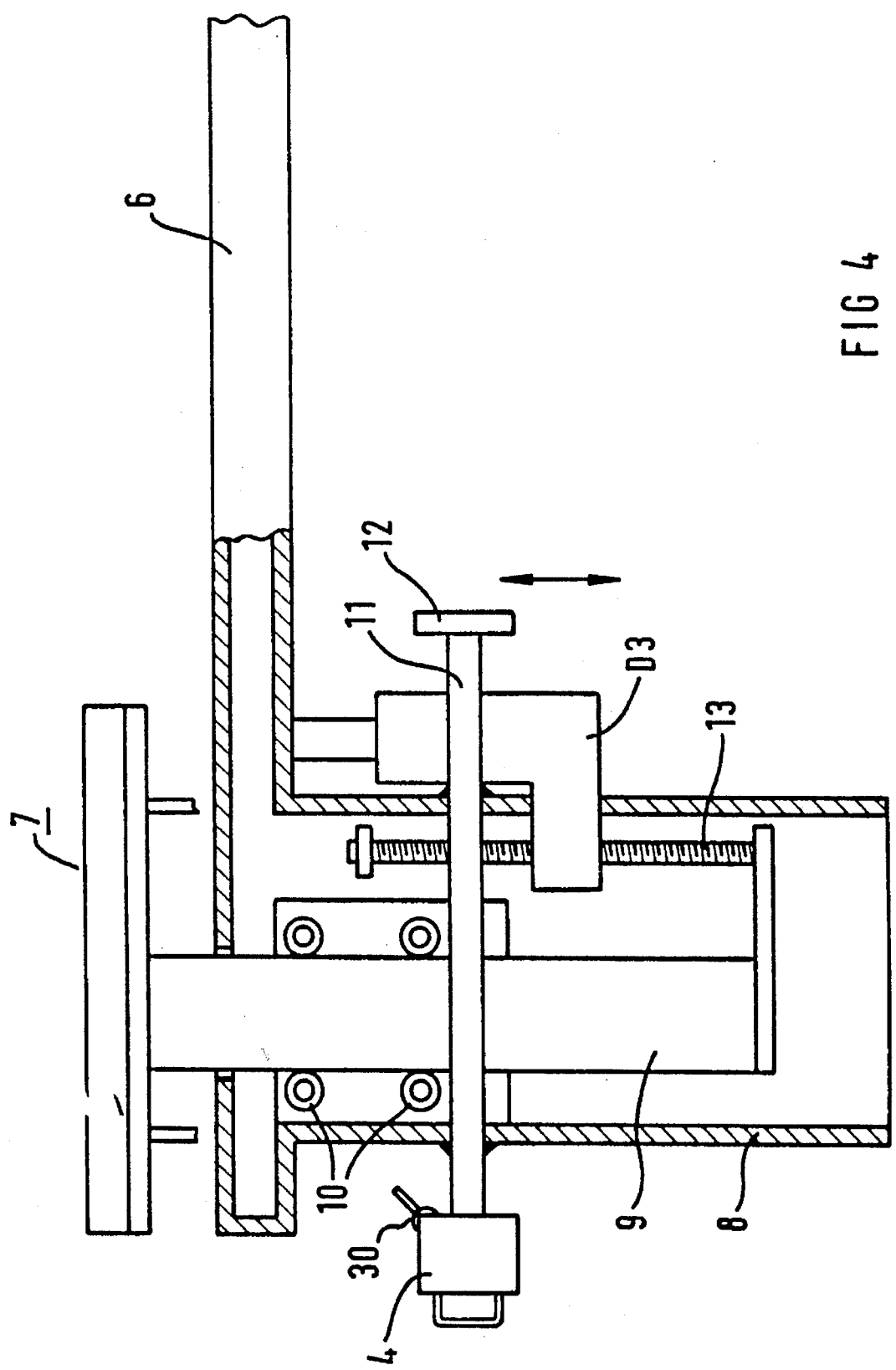
FIG. 4 shows the apparatus of FIG. 3 in a front view, partially in section.

As may be seen from FIG. 4, which shows the apparatus in a front view and partially in section, a threaded spindle 13 that cooperates with a geared motor generally referenced D3 is located at the blade 9 that carries the head-holder 7 and positioning means. The geared motor D3 is secured either to the housing 8 or to the boom 6. As shall be set forth in greater detail below, what is achieved with the assistance of the illustrated adjustment arrangement having the drive D3 permits the head-holder 7 and positioning means to effectively execute no motion during the ceph exposure, i.e., it is held stationarily in space, when the x-source 3 together with the line camera 4 are vertically moved.

Figure 5:
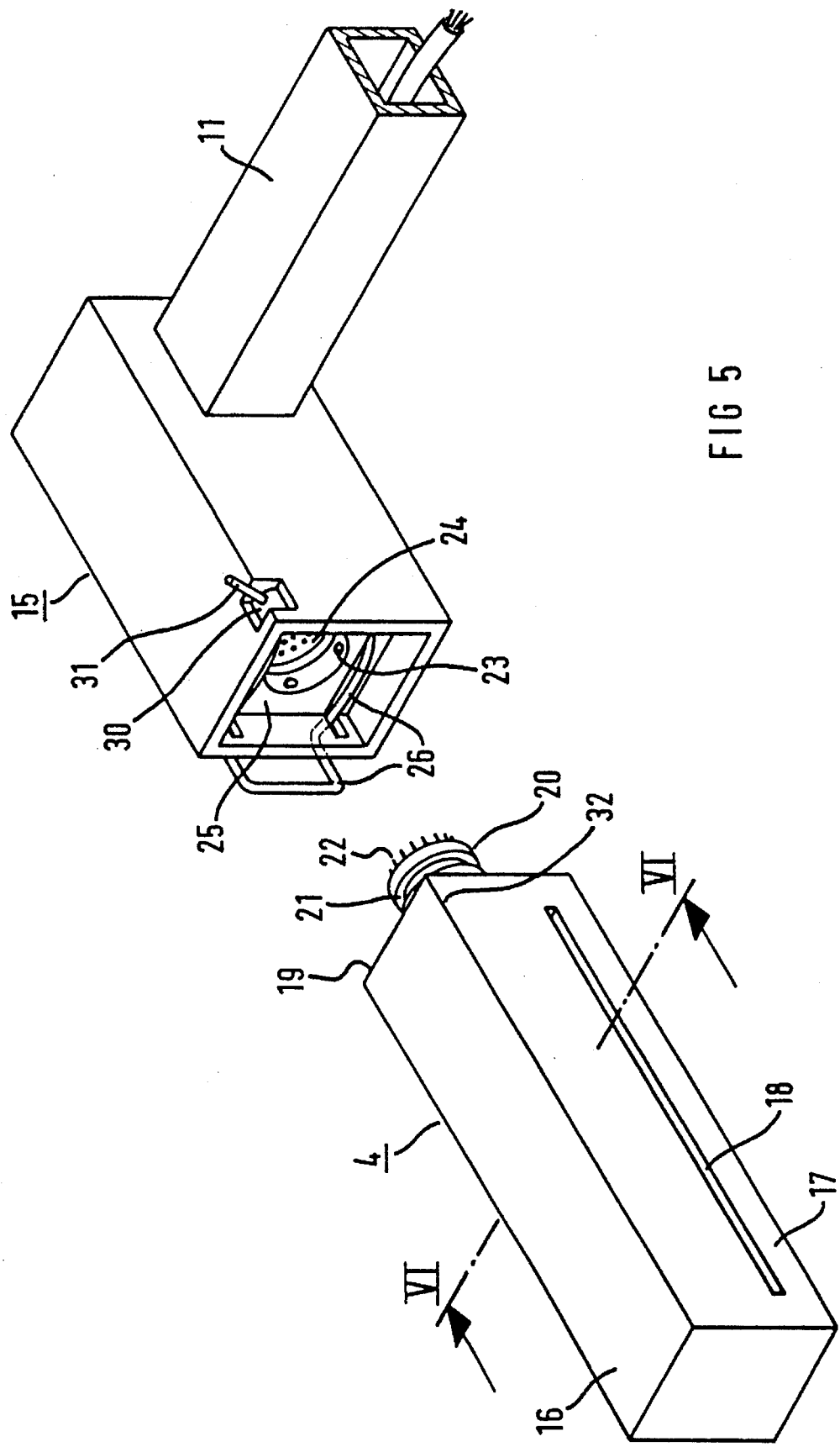
FIG. 5 is an embodiment of a line detector camera and its holder constructed in accordance with the principles of the present invention, in a schematic, exploded view.

FIG. 5 shows a schematic, exploded view of, first, the line camera 4 and, second, a holder 15 that is secured to the traverse element 11 for the embodiment of FIG. 2. In the case of the version of FIG. 1 (for PAN exposures), an identically fashioned holder (but without the traverse element 11) is vertically secured to the rotatory unit 2 (FIG. 1).

The line camera 4 contains an oblong housing 16 that is composed of a rectangular tube in the exemplary embodiment and that has a slot 18 in the front lateral surface 17 facing toward the radiation source 3. The slot 18 is located in the lower third of the lateral surface 17, as a result of which the line camera can be moved into a comparatively low initial position (see the broken-line illustration in FIG. 2).

Figure 6:
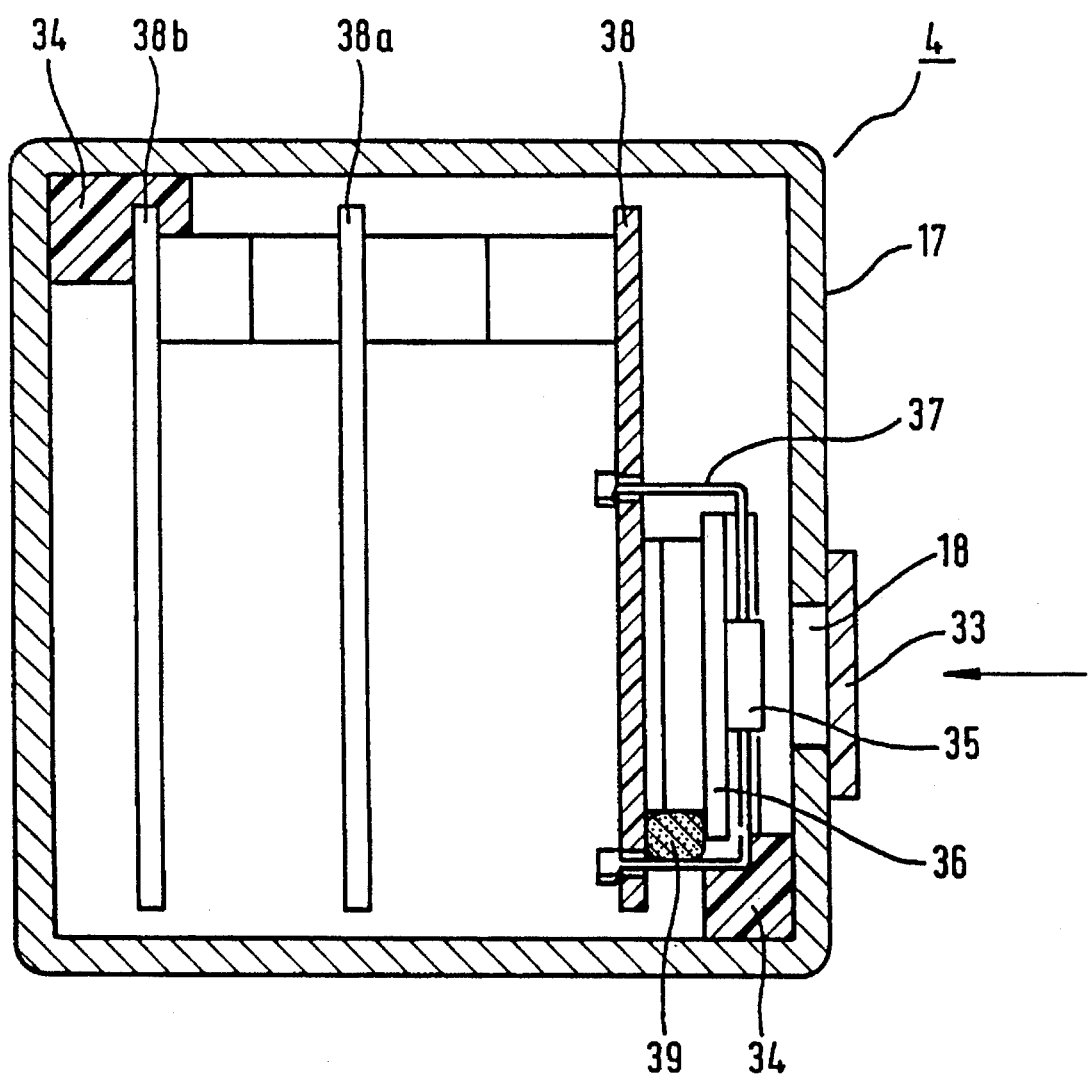
FIG. 6 shows the line detector camera in cross-section along the line VI—VI in FIG. 5.

As proceeds in further detail from FIG. 6, a radiation-sensitive line detector in the form, for example, of a CCD sensor is located behind the slot 18 in the inside of the profiled tube 16. A peg-shaped connector element 20 forming mechanical and electrical connector means to the holder 15 is located at the one face side 19. The mechanical connector means include an annular channel 21 that cooperates with a ball catch 23. The electrical connector means are composed of a multi-pin plug 22 that interacts with a socket 24 in the holder 15. The pins of the plug 22 are connected to the aforementioned line detector and to further electronics located in the inside of the line camera 4. The holder 15 is constructed such that the face side 19 of the line camera 4 resides opposite an end face connecting surface 25 of the holder 15 when the line detector is put in place.

There are no other mechanical connections between the line camera 4 and the holder 15. The line camera 4 can thus be easily manually detached from the holder 15. As used herein, the term "manually detached" means that the line camera 4 can be separated from the holder 15 simply by manually exerting a pulling force between the holder 15 and the line camera 4.

An ejector mechanism 26 is provided so that the release of the line camera 4 from the holder 15 is facilitated, particularly to prevent tilting, and thus the risk of damage to the highly sensitive electrical contacts. This ejector mechanism 26 in the present embodiment is composed of a shackle that is conducted to the outside in a slot of the housing wall of the holder 15. When the shackle is actuated with the line camera in place, adjacent shackle parts press against the end face 19 and thus exert a central force on the surface, as a result of which the connection can be easily released.

A centering mechanism 30 that includes a lever 31 is eccentrically seated in the housing of the holder. After the introduction of the line camera 4 into the holder 15, the lever 31 is actuated, as a result of which a surface of the eccentrically seated mechanism 30 presses against an edge 32 of the housing and holds said housing in a defined, reproducible position. Even though the housing is fashioned of one part in the present exemplary embodiment, the housing can alternatively be formed by multiple parts, whereby the housing part that carries the detector is then centered in the aforementioned way. The detector can thus be fixed with reference to the holder independently of the camera housing and the possible mounting and fabricating tolerances thereof.

The fundamental structure of the line camera proceeds from FIG. 6, which shows a section along the line VI, VI in FIG. 5. The housing is fashioned light-tight; the slot 18 has its end face covered by a light-opaque but x-ray-transmissive plastic plate 33. A CCD sensor 35 provided with a preceding scintillation layer, and possibly, with intervening fiber optics, is located in the inside behind this plastic plate 33. The CCD sensor 35 can be fashioned of one piece or can be multi-part and can be advantageously fashioned as a sensor matrix of amorphous silicon. A metallic holder 37 connects the carrier 36 and the CCD element 35 to a circuit board 38. Flexible contact strips 39, for example of silicone provided with gold fibers, effect the electrical contact between the sensor 35 and the circuit board 38. The circuit board 38 contains all components directly required for the drive of the CCD sensor 35. As warranted, further circuit boards 38a and 38b can be arranged in the housing. The lines departing from the circuit board or boards 38, or 38a and 38b lead to the aforementioned pins of the plug 22 (FIG. 5). Shock-absorbing elements 34 bear the detector 35 and the control boards 38, 38a and 38b in a "floating" manner in the housing. The highly sensitive and expensive parts can thus be largely protected against breakage or release of the contact connections given an unintentional dropping of the camera.

As initially mentioned, the same basic apparatus and the same camera can be employed for PAN exposures (FIG. 1) and for ceph exposures (FIG. 2). In order to achieve the image size needed for a ceph exposure, the line camera advantageously has a correspondingly longer sensor. The line camera can thus be attached either to the ceph or to the PAN holder as needed. Various possibilities for holding the line camera at the holder 15 are conceivable. Instead of the illustrated ball catch, a bayonet-type connection can also be provided. Likewise, some other external shape instead of a rectangular profile can be provided for the housing of the line camera.

The following should be noted regarding the exposure principle. A PAN tomogram is achieved in such a way that the signals acquired when sweeping the subject (jaw) to be registered are added up in the two-dimensionally resolving detector; the adding of the signals—if a CCD sensor is employed—can already be implemented within the sensor by operating in that the sensor in the TDI mode. The function of a moving film is simulated by this special operating mode, in that the charge packets generated by exposure are corresponding clocked in the CCD element, whereas new charges are continuously added thereto. The clock pulses for the TDI mode are derived from the stepping motor pulses which would otherwise be required for the film cassette drive.

Alternatively, an accumulation in a later signal processing stage is possible.

The ceph exposure is likewise carried out in slot technique. The head of a standing (or seated) patient is swept from top to bottom (given a horizontal arrangement), or from left to right (given a vertical arrangement) and vice versa, with a ray fan dependent on the arrangement of the line camera. Adjusted by the aforementioned pre-diaphragm 11, this ray fan exactly impinges the horizontally arranged slot of CCD sensor. With the assistance of the drive D1, the overall apparatus, i.e. the x-ray source 3 with primary and secondary diaphragms as well as line camera 4 with sensor, is then displaced vertically proceeding from an initial position (see the arrows in FIG. 2). Simultaneously, the head-holder 7 and positioning means is moved in the opposite direction with the assistance of the drive D3, whereby the two motions are matched such to one another so that the patient's head remains spatially fixed, i.e. stationary. The control of the two drive motors D1 and D3 ensues via a microprocessor 40 according to the block circuit diagram of FIG. 7. Speed recognition sensors 41, direction sensing switches 42 and 43, as well as a limit switch 44 and a correction switch 45 are respectively allocated to the two drives. The control, which ensues via pulse-width modulation, also contains safety switches 46. Evaluation electronics of the microcontroller 40 recognizes which holder (PAN or ceph device) to which the camera is secured. When a ceph exposure is selected, the drive motor D3 moves into the initial position, for example, into the lower adjustment position (broken-line position in FIG. 2). The limit switch 44 responds in this position. The head-holder positioning means can now be set to the size of the patient by height adjustment of the carrying column 1. During the ceph exposure, the drive motor D3 moves the head holder 7 upwardly, whereas the drive motor D1 for the carrying column simultaneously moves downwardly. The two drives are thereby controlled such that the difference between the adjustment speeds is equal to zero. It is thus assured that the distance of the ear button, and thus of the head position from the floor remains constant. The exposure is ended when the limit switch 44 or a system clock counter (TDI clock-counter) recognizes the upper limit position.

For example, the TDI clock for the CCD sensor 36 is derived from the drive motor D1 that is provided for the height adjustment of the carrying column. Alternatively, it can also be acquired from the signals of a position that directly measures the adjustment of the carrying column. Differing from a PAN exposure, the TDI mode herein does not serve the purpose of producing a blurring and, thus, a tomogram, but serves the purpose of utilizing the full width of the sensor for the creation of the image. Here, thus, the TDI mode produces an exposure corresponding to that which would be obtained if a film were moved relative to the slot.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray diagnostics installation comprising:

an x-ray source;

a line detector camera;

holder means, to which said x-ray source and said line detector camera are mounted opposite and spaced from each other a distance adapted to accommodate a human skull, for moving said x-ray source and said line detector camera relative to the skull with the skull remaining stationary, for recording an x-ray exposure with said line detector camera;

said line detector camera generating electrical output signals dependent on x-rays from said x-ray source, said line detector camera having an elongated housing having a surface facing said x-ray source, said surface having a longitudinally extending slot therein for the entry of x-rays, an x-ray sensitive detector disposed behind said slot, said detector having a plurality of detector elements arranged to form at least one line, each detector element having a contact connected to at least one control line, each control line being connected to a connector part disposed at an end of said housing, and said connector part a plurality of electrical connections and manually operable mechanical connector means for releasably connecting said line detector camera to said holder means, said mechanical Connector means comprising the only mechanical connection between said detector camera and said holder means and permitting said line detector camera to be manually pulled away from said holder to release said mechanical connector means.

2. An x-ray diagnostics installation as claimed in claim 1, wherein said connector part further includes an interlock mechanism for preventing unintentional release of said line detector camera from said holder means.

3. An x-ray diagnostics installation as claimed in claim 1, wherein at least one of said housing and said holder means contain centering means for fixing said housing in a defined position relative to said holder means.

4. An x-ray diagnostics installation as claimed in claim 3, wherein said centering means comprises said housing and said holder means having mating shapes permitting only one orientation of said housing relative to said holder means.

5. An x-ray diagnostics installation as claimed in claim 1, wherein said housing is a multi-cornered tube having an end face at which said connector is disposed.

6. An x-ray diagnostics installation as claimed in claim 1, wherein said holder includes ejection means, interacting with said end face of said housing, for axially releasing said end face from said holder means upon actuation of said ejection means.

7. An x-ray diagnostics installation as claimed in claim 1, wherein said housing has a longitudinal length approximately corresponding to the width of a human skull, wherein said x-ray detector comprises a CCD sensor having a scintillator layer disposed thereon inside said housing, and said line detector camera further including at least one electrical control circuit board for driving said CCD sensor electrically connected to said CCD sensor and contained in said housing.

8. An x-ray diagnostics installation as claimed in claim 7, wherein said line detector camera further includes a carrier for said CCD sensor attached to said circuit board with a retainer clamp.

9. An x-ray diagnostics installation as claimed in claim 7, wherein said line detector camera further includes shock-absorbing damping means for mounting said circuit board in said housing.

10. An x-ray diagnostics installation as claimed in claim 1, wherein said line detector camera further includes shock-absorbing damping means for mounting said detector in said housing.

11. An x-ray diagnostics installation as claimed in claim 1, wherein said housing of said line detector camera comprises a rectangular hollow tube having a square cross section.

12. An x-ray diagnostics installation as claimed in claim 1, further comprising safety catch means attached to said holder means for preventing unintentional dropping of said line detector camera after release from said connector means.

13. An x-ray diagnostics installation as claimed in claim 1, wherein said x-ray source, said holder means and said line detector camera comprise, in combination, means for generating a PAN exposure of an examination subject as said x-ray exposure.

14. An x-ray diagnostics installation as claimed in claim 1, wherein said x-ray source, said holder means and said line detector camera comprise, in combination, means for generating a ceph exposure of an examination subject as said x-ray exposure.

* * * * *